United States Patent
Taniguchi et al.

(10) Patent No.: US 12,143,755 B2
(45) Date of Patent: Nov. 12, 2024

(54) ENDOSCOPE SYSTEM, AND IMAGE PROCESSING APPARATUS AND IMAGE PROCESSING METHOD USED IN ENDOSCOPE SYSTEM

(71) Applicant: OLYMPUS CORPORATION, Tokyo (JP)

(72) Inventors: Katsuyoshi Taniguchi, Hino (JP); Yamato Kanda, Hino (JP); Akihiro Kubota, Kokubunji (JP)

(73) Assignee: OLYMPUS CORPORATION, Tokyo (JP)

( * ) Notice: Subject to any disclaimer, the term of this patent is extended or adjusted under 35 U.S.C. 154(b) by 687 days.

(21) Appl. No.: 17/239,802

(22) Filed: Apr. 26, 2021

(65) Prior Publication Data

US 2021/0241457 A1    Aug. 5, 2021

Related U.S. Application Data

(63) Continuation of application No. PCT/JP2018/040315, filed on Oct. 30, 2018.

(51) Int. Cl.
*H04N 7/18* (2006.01)
*A61B 1/00* (2006.01)
(Continued)

(52) U.S. Cl.
CPC ....... *H04N 7/185* (2013.01); *A61B 1/000096* (2022.02); *G06T 1/20* (2013.01);
(Continued)

(58) Field of Classification Search
CPC ............ H04N 7/185; H04N 5/38; H04N 7/18; H04N 23/555; A61B 1/000096;
(Continued)

(56) References Cited

U.S. PATENT DOCUMENTS

| | | | |
|---|---|---|---|
| 2008/0275315 A1* | 11/2008 | Oka | A61B 5/445 705/3 |
| 2018/0047165 A1 | 2/2018 | Sato | |
| 2018/0060512 A1* | 3/2018 | Sorenson | G06Q 10/06398 |
| 2018/0114319 A1* | 4/2018 | Kono | A61B 1/018 |

(Continued)

FOREIGN PATENT DOCUMENTS

| | | |
|---|---|---|
| EP | 3318176 A1 | 5/2018 |
| JP | 2008-124591 A | 5/2008 |

(Continued)

OTHER PUBLICATIONS

International Search Report dated Jan. 15, 2019 issued in PCT/JP2018/040315.

*Primary Examiner* — Fayyaz Alam
(74) *Attorney, Agent, or Firm* — Scully, Scott, Murphy & Presser, P.C.

(57) ABSTRACT

An image processing device includes: a first processor configured to perform image processing on an inputted image, the image processing including diagnostic process; a second processor configured to perform selection processing to select and transmit a portion of the inputted image to an external image processing apparatus connected to an external network; and an interface configured to receive a processing result of the diagnostic process by the external image processing apparatus.

21 Claims, 7 Drawing Sheets

(51) Int. Cl.
*G06T 1/20* (2006.01)
*G06T 7/00* (2017.01)
*H04N 5/38* (2006.01)
*H04N 23/50* (2023.01)

(52) U.S. Cl.
CPC ............. *G06T 7/0012* (2013.01); *H04N 5/38* (2013.01); *H04N 7/18* (2013.01); *G06T 2207/10068* (2013.01); *G06T 2207/30096* (2013.01); *H04N 23/555* (2023.01)

(58) Field of Classification Search
CPC ...................... G06T 1/20; G06T 7/0012; G06T 2207/10068; G06T 2207/30096; G06T 2200/28; G06T 2207/10016; G06T 2207/20016; G16H 30/40
See application file for complete search history.

(56) References Cited

U.S. PATENT DOCUMENTS

| | | | |
|---|---|---|---|
| 2018/0137244 A1* | 5/2018 | Sorenson | A61B 8/565 |
| 2021/0050094 A1* | 2/2021 | Orringer | G01N 21/65 |
| 2023/0293132 A1* | 9/2023 | Liu | A61B 6/5211 |
| | | | 382/103 |

FOREIGN PATENT DOCUMENTS

| | | |
|---|---|---|
| JP | 2009-169244 A | 7/2009 |
| JP | 2009-178180 A | 8/2009 |
| JP | 2013-128702 A | 7/2013 |
| JP | 2014-128423 A | 7/2014 |
| WO | 2017/002184 A1 | 1/2017 |
| WO | 2017/006574 A1 | 1/2017 |
| WO | 2017/199635 A1 | 11/2017 |

* cited by examiner

ENDOSCOPE SYSTEM, AND IMAGE PROCESSING APPARATUS AND IMAGE PROCESSING METHOD USED IN ENDOSCOPE SYSTEM

CROSS REFERENCE TO RELATED APPLICATION

This application is a continuation application of PCT/JP2018/040315 filed on Oct. 30, 2018, the entire contents of which are incorporated herein by this reference.

BACKGROUND OF THE INVENTION

1. Field of the Invention

The present invention relates to an endoscope system capable of cooperative processing with an apparatus on a network, and to an image processing apparatus and an image processing method used in the endoscope system.

2. Description of the Related Art

In related art, computer-aided diagnosis (CAD) is developed to process medical images and thereby provide support information such as by providing quantitative decision scales, identifying microstructures to focus on during diagnosis, and providing estimation results regarding the state of a disease through image analysis. For example, CAD is used to make diagnoses from X-ray images.

Also, in recent years, a CAD system that indicates the position of a lesion candidate and displays differentiating information with respect to a moving image obtained from an endoscope has also been announced. Displaying differentiating information in CAD requires enormous computation. Consequently, from the perspective of computing power, only a system disposed in an operating room for example may be incapable of making a conclusive diagnosis through CAD, or making a conclusive diagnosis may be enormously time-consuming in some cases. Accordingly, it is conceivable to transmit image information and the like over a network to external equipment having a large amount of processing power, and perform a diagnostic process in the external equipment.

In this case, it is also conceivable to perform an image encoding process to reduce the transmission volume. For example, Japanese Patent Application Laid-Open Publication No. 2008-124591 discloses a technology that reduces the amount of data transmitted in a monitoring camera system provided with a plurality of cameras by encoding image information to reduce the image information flowing to the system over a network.

SUMMARY OF THE INVENTION

An image processing apparatus used in an endoscope system according to one aspect of the present invention includes: a first processor configured to perform image processing on an inputted image, the image processing including diagnostic process; a second processor configured to perform selection processing to select and transmit a portion of the inputted image to an external image processing apparatus connected to an external network; and an interface configured to receive a processing result of the diagnostic process by the external image processing apparatus.

An endoscope system according to another aspect of the present invention includes the image processing apparatus used in the endoscope system, and the external image processing apparatus.

An image processing method used in an endoscope system according to another aspect of the present invention includes: performing image processing on an inputted image, the image processing including diagnostic process; performing selection processing to select and transmit a portion of the inputted image to an external image processing apparatus connected to an external network; and receiving a processing result of the diagnostic process by the external image processing apparatus.

DETAILED DESCRIPTION OF THE PREFERRED EMBODIMENTS

Hereinafter, embodiments of the present invention will be described in detail and with reference to the diagrams.

First Embodiment

Figure 1:
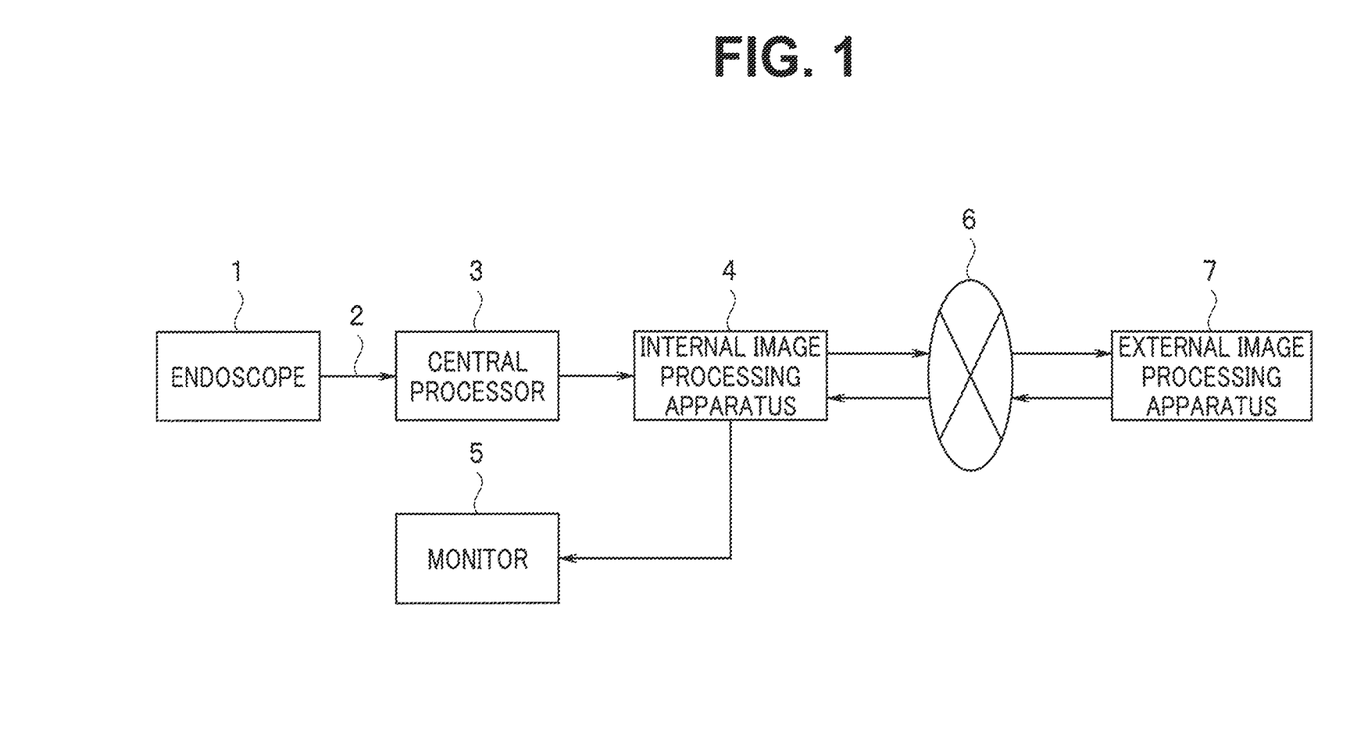
FIG. 1 is an explanatory diagram illustrating an endoscope system using an image processing apparatus according to a first embodiment of the present invention.

FIG. 1 is an explanatory diagram illustrating an endoscope system using an image processing apparatus according to a first embodiment of the present invention.

The endoscope system according to the present embodiment includes an internal image processing apparatus disposed on the internal side of an external network, and an external image processing apparatus that is accessible through the external network by the internal image processing apparatus. Generally, whereas the external image processing apparatus connected to the external network has high processing power compared to the internal image processing apparatus and performs high-precision processing easily in many cases, the internal image processing apparatus disposed on the internal side of the external network can perform processes more quickly by a time period corresponding to the amount of time taken to access and transmit data on the external network, and is capable of high-speed processing and real-time processing as a result.

In consideration of such advantages of the internal image processing apparatus and the external image processing apparatus, the present embodiment selectively transmits image information and the like used in processing to the external image processing apparatus, thereby reducing the transmission volume and at the same time enabling detailed, reliable, and conclusive processing while also securing real-time performance and high-speed performance, as necessary.

The present embodiment will be described by taking a moving image obtained from an endoscope as an example of an image to be processed, but the present embodiment is not limited to medical images such as endoscopic images, and is applicable to the processing of various types of moving images. Also, an apparatus that adopts a medical image as the image of application and performs a diagnostic process and the like as image processing is described as an example, but the type of image processing is not particularly limited, and is applicable to various types of image processing.

In FIG. 1, an endoscope 1 has an elongated insertion portion not illustrated that is inserted into a body cavity, and an operation portion (not illustrated) operated by an operator is coupled to a proximal end portion of the insertion portion. A universal cord 2 extends from the operation portion and is connected to a central processor 3. An illumination lens configured to illuminate an observation target is provided in a distal end portion of the insertion portion of the endoscope 1, such that a subject is irradiated with illuminating light through the illumination lens. Reflected light from the subject is introduced into the insertion portion through an objective lens provided in the distal end of the insertion portion, and incident on an image pickup portion including a sensor such as a CCD or CMOS sensor provided in the endoscope 1. The image pickup portion outputs an image pickup signal based on the optical image of the subject to the central processor 3 through the universal cord 2.

The central processor 3 performs predetermined signal processing on the image pickup signal from the endoscope 1 to generate an endoscopic image in a format that is displayable on a monitor 5. The central processor 3 outputs the generated endoscopic image (medical image) to an internal image processing apparatus 4. Note that although an example is illustrated in which only an endoscopic image obtained by the endoscope 1 is inputted into the internal image processing apparatus 4, multiple types of medical images may also be inputted, such as images from a plurality of endoscopes and images from an endoscopic ultrasound scope.

The internal image processing apparatus 4 is capable of providing diagnostic support through image analysis of inputted medical images. For example, the internal image processing apparatus 4 can detect lesion candidates on the basis of medical images. As another example, the internal image processing apparatus 4 may be capable of differentiating detected lesion candidates, such as whether a lesion candidate is benign or malignant.

Any of various known methods can be adopted in the detection and differentiation of lesion candidates by the internal image processing apparatus 4. For example, the internal image processing apparatus 4 may detect and differentiate lesion candidates by machine learning using AI. For example, the internal image processing apparatus 4 may generate an inference model configured to detect and differentiate lesion candidates from medical images through deep learning using a large number of training images, such as images of lesions and images of things other than lesions. In this case, the internal image processing apparatus 4 can output information about the probability of a lesion candidate and the probability of differentiation.

Note that any of various known networks may be adopted as the network to adopt for machine learning. For example, regions with convolutional neural network (CNN) features (R-CNN) or a fully convolutional network (FCN) using a CNN may be used. Furthermore, not only deep leaning, any of various machine learning techniques may be adopted to acquire an inference model.

In addition, the internal image processing apparatus 4 may also detect and differentiate lesion candidates from medical images according to a method other than machine learning. For example, the internal image processing apparatus 4 may detect and differentiate lesion candidates by determining respective image portions regarding properties such as color, shapes such as projections, and surface shapes through image analysis of medical images.

The internal image processing apparatus 4 is capable of accessing an external network 6 and exchanging information with an external image processing apparatus 7 connected to the external network 6. Note that the external network 6 may be a public network such as the Internet, or a hospital network for example.

The external image processing apparatus 7 has functions similar to the internal image processing apparatus 4, and is capable of high-precision processing in a relatively short time period compared to the internal image processing apparatus 4. For example, in the case where the diagnostic functions of the external image processing apparatus 7 are achieved by machine learning, the external image processing apparatus 7 performs machine learning using a greater number of images, and is capable of making reliable and accurate diagnoses compared to the internal image processing apparatus 4. Note that the external image processing apparatus 7 is not limited to achieving functions with a single computer and may also achieve functions with a plurality of computers performing distributed processing, and furthermore may also achieve cloud computing that provides various functions as services over the Internet.

The internal image processing apparatus 4 can not only make diagnoses locally, but also request a diagnosis or the like by transmitting image information and the like to the external image processing apparatus 7. In this case, in the present embodiment, the internal image processing apparatus 4 selects the image information and the like to provide to the external image processing apparatus 7 from among inputted image information, and outputs only a portion of the image information to the external image processing apparatus 7. The external image processing apparatus 7, obeying the request from the internal image processing apparatus 4, can make a diagnosis with respect to the received image information, and transmit a diagnostic result to the internal image processing apparatus 4 over the external network 6.

The internal image processing apparatus 4 can output a medical image from the central processor 3 to the monitor 5. Also, the internal image processing apparatus 4 can generate monitor output to display a diagnostic result by the internal image processing apparatus 4 and a diagnostic result from the external image processing apparatus 7, and output the monitor output to the monitor 5. Note that the internal image processing apparatus 4 is capable of causing a diagnostic result to be displayed on the monitor 5 superimposed onto a medical image from the central processor 3.

In the present embodiment, the internal image processing apparatus 4 selects image information to provide to the external image processing apparatus 7 on the basis of a selection signal from an outside. For example, a signal based on an operation of the endoscope 1 can be used as the selection signal from the outside.

For example, the operation portion of the endoscope 1 is provided with a release switch operated to photograph a still image, a freeze switch operated to display a still image and the like. The release switch and the freeze switch are thought to be operated in the case where surgeon decides that careful observation is necessary, for example. Accordingly, when the release switch or the freeze switch is operated, an operation signal based on the operation may be supplied to the internal image processing apparatus 4 as a selection signal for selecting the output destination of the image information. When a selection signal based on an operation of the release switch or the freeze switch is inputted, the internal image processing apparatus 4 supplies a still image specified by the operation to the external image processing apparatus 7 over the external network 6.

Additionally, the endoscope 1 is not only capable of normal light observation using visible light (white light imaging: WLI), but is also capable of special light observation such as narrow band light observation (narrow band imaging: NBI) and autofluorescence imaging (AFI). The operation portion of the endoscope 1 is also provided with a switch operated to select the normal light observation and the special light observation, and an operation signal based on the operation of the switch may be supplied to the internal image processing apparatus 4 as a selection signal for selecting the output destination of the image information. In this case, the internal image processing apparatus 4 itself uses the image information inputted during the normal light observation, and when a selection signal based on an operation specifying the special light observation is inputted, the internal image processing apparatus 4 supplies inputted images to the external image processing apparatus 7 over the external network 6.

Also, although switching the observation mode is given as an example of an operation, an operation of scrutinizing an image, such as an operation signal for enlarging the image, may also be adopted as a selection signal. Additionally, a case such as when the image is stopped for a predetermined time period or longer may also be detected and treated as a selection signal.

Note that an operation signal based on an operation of the endoscope 1 may be supplied to the central processor 3 and then supplied to the internal image processing apparatus 4 as a selection signal from the central processor 3, or alternatively may be supplied directly from the endoscope 1 to the internal image processing apparatus 4.

Also, various types of medical equipment may be provided inside an examination room, and a signal based on the operation of a switch that turns on or turns off a piece of medical equipment, such as an electric scalpel or a footswitch, may be supplied to the internal image processing apparatus 4 as a selection signal. In this case, it is possible to perform a selection process such as transmitting image information to the external image processing apparatus 7 when the footswitch is used, for example.

Figure 2:
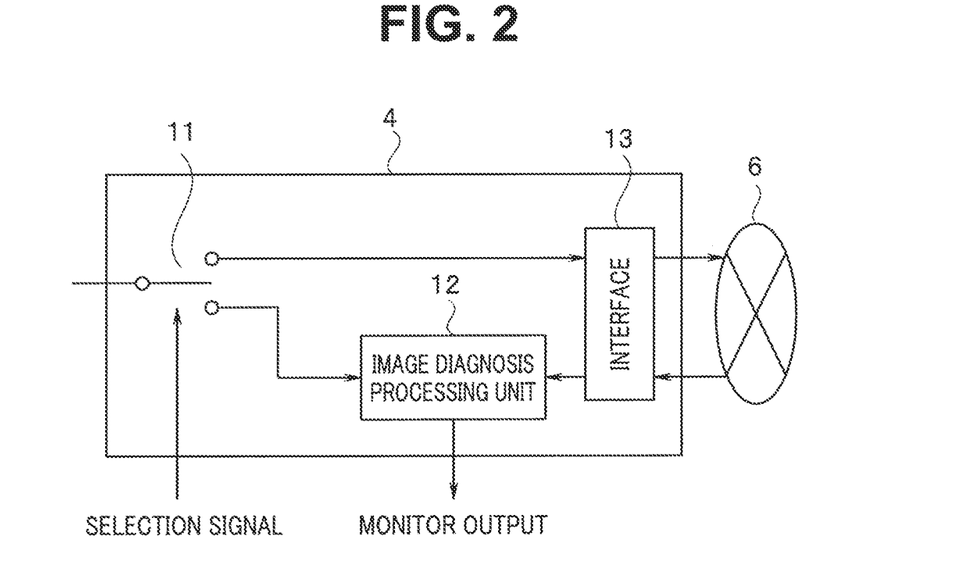
FIG. 2 is a block diagram illustrating an example of a specific configuration of an internal image processing apparatus 4.

FIG. 2 is a block diagram illustrating an example of a specific configuration of the internal image processing apparatus 4.

The internal image processing apparatus 4 includes a switch 11, an image diagnosis processing unit 12, and an interface 13. A medical image or the like is inputted from the central processor 3 into the switch 11 that acts as a selection processing unit, and the inputted medical image is outputted to the interface 13 or to the image diagnosis processing unit 12 on the basis of a selection signal. The image diagnosis processing unit 12 that acts as an internal image processing unit may include a processor using a central processing unit (CPU), a field-programmable gate array (FPGA), or the like, and may control each unit by operating according to a program stored in a memory not illustrated, or achieve some or all functions in a hardware electronic circuit. The image diagnosis processing unit 12 executes a diagnostic process adopting the machine learning described above or some other methods on the input medical image, and outputs a diagnostic result to the monitor 5 as monitor output. The interface 13 is capable of exchanging information between the internals of the internal image processing apparatus 4 and the external network 6, transmitting a medical image or the like from the switch 11 to the external image processing apparatus 7 over the external network 6 and also receiving and supplying information from the external image processing apparatus 7 over the external network 6 to the image diagnosis processing unit 12.

Next, operations by the embodiment configured as above will be described.

Assume that the endoscope 1 is inserted into a subject, and an endoscopic image is used to detect and differentiate a lesion inside the subject. The surgeon inserts the insertion portion not illustrated into the subject not illustrated. The endoscope 1 outputs an image pickup signal acquired by shooting inside the subject to the central processor 3. The central processor 3 generates an endoscopic image based on the image pickup signal from the endoscope 1, and outputs the endoscopic image to the internal image processing apparatus 4.

The internal image processing apparatus 4 supplies the inputted endoscopic image to the image diagnosis processing unit 12 according to the switch 11 in FIG. 2, for example. The image diagnosis processing unit 12 can supply the inputted endoscopic image to the monitor 5 and cause the inputted endoscopic image to be displayed on a display screen of the monitor 5. Additionally, the image diagnosis processing unit 12 performs a diagnostic process on the endoscopic image and supplies a diagnostic result to the monitor 5 as monitor output. With the above, the diagnostic result from the image diagnosis processing unit 12 is displayed together with the endoscopic image from the central processor 3 on the display screen of the monitor 5.

Because of limitations in processing performance, the image diagnosis processing unit 12 is not necessarily capable of performing an accurate and precise diagnosis with real-time processing of the endoscopic image. Accordingly, in general, the image diagnosis processing unit 12 is used only to detect lesion candidates, for example. The image diagnosis processing unit 12 performs a diagnostic process using machine learning for example, and detects whether or not a lesion candidate exists in the endoscopic image. When a lesion candidate is detected in the endoscopic image, the image diagnosis processing unit 12 outputs a detection result to the monitor 5 as monitor output. In this way, a display indicating that a lesion candidate has been detected and a display indicating the position of the lesion candidate are superimposed onto the endoscopic image and displayed on the display screen of the monitor 5 together with the endoscopic image.

From the display on the monitor 5, the surgeon recognizes that a lesion candidate has been detected. Subsequently, to conclusively detect and differentiate the lesion, the surgeon operates the release switch for example while keeping the lesion candidate inside the shooting range of the endoscope 1. With the above operation, the endoscope 1 outputs an image pickup signal of a still image to the central processor 3, and the central processor 3 outputs a still image to the internal image processing apparatus 4. On the other hand, an operation signal based on the release switch operation is supplied to the switch 11 of the internal image processing apparatus 4 as a selection signal. With the above, the switch 11 changes the output destination of the inputted endoscopic still image containing a lesion candidate position to the interface 13. In this way, the endoscopic still image containing the lesion candidate position is outputted from the interface 13 to the external image processing apparatus 7 over the external network 6.

Note that an example is described in which an image is transmitted to the external image processing apparatus by having the user press the release switch after a lesion candidate is detected, but an image may also be transmitted as a trigger of the detection of the lesion candidate itself.

The external image processing apparatus 7 performs a diagnostic process on the inputted endoscopic still image. The external image processing apparatus 7 is capable of high-performance processing, and can make an accurate and precise diagnosis in some cases. Through the diagnostic process performed on the still image containing a lesion candidate, the external image processing apparatus 7 determines whether or not the lesion candidate is a lesion, and also differentiates the lesion if possible. The external image processing apparatus 7 outputs a lesion detection result and differentiation result to the internal image processing apparatus 4 over the external network 6.

The interface 13 of the internal image processing apparatus 4 receives and supplies the diagnostic result from the external image processing apparatus 7 to the image diagnosis processing unit 12. The image diagnosis processing unit 12 outputs the reliable diagnostic result from the external image processing apparatus 7 to the monitor 5 as monitor output. In this way, an endoscopic image is displayed on the display screen of the monitor 5 together with a display indicating whether or not a lesion exists in the endoscopic image, and if a lesion does exist, a display indicating the position of the lesion is also displayed. Furthermore, in the case where a differentiation result is obtained by the external image processing apparatus 7, a display indicating the lesion differentiation result is also displayed on the display screen of the monitor 5.

Note that the information transmitted from the external image processing apparatus 7 as the diagnostic result may include not only a result (1 or 0) indicating whether the target image is benign or malignant and a numerical value (a numerical value from 0 to 1) indicating the probability of malignancy, but may also include display data such as a graphical representation of the diagnostic result, for example. In this case, the image diagnosis processing unit 12 may output the received diagnostic result directly to the monitor 5. It is also possible to supply transmission data from the external image processing apparatus 7 to the monitor 5 directly without going through the image diagnosis processing unit 12. Also, the image diagnosis processing unit 12 may cause a frame indicating a lesion detection result to be displayed on the monitor 5 with the color or shape of the frame changed on the basis of the received information.

In this way, if the internal image processing apparatus 4 detects a lesion candidate during an examination using an endoscope, a display related to the lesion candidate can be displayed on the display screen of the monitor 5. The internal image processing apparatus 4 is provided on the internal side of the external network 6, and therefore can receive image information in a short time period and additionally execute a diagnostic process that is processable in a relatively short time period, and cause a diagnostic result to be displayed in real-time, for example. The surgeon checks the display indicating that a lesion candidate exists during an examination, and performs some kind of operation causing an endoscopic image to be transmitted to the external image processing apparatus 7. With the above, by using the switch 11 to transmit an endoscopic image to the external image processing apparatus 7 over the external network 6, a precise (detailed) and reliable diagnostic result is obtained in the external image processing apparatus 7. The diagnostic result is supplied to the internal image processing apparatus 4 over the external network 6 and displayed on the display screen of the monitor 5. In this way, the surgeon is able to recognize a reliable and detailed diagnostic result from the display of the monitor 5 after a predetermined amount of time from the operation of the release switch or the like during an examination, for example. Also, only necessary information is transmitted to the external image processing apparatus 7, and the amount of transmitted data can be reduced.

In this way, in the present embodiment, image information to be transmitted to an external image processing apparatus is selected on the basis of a selection signal according to an operation by the surgeon for example, and the amount of data transmitted to the external image processing apparatus can be reduced. Additionally, the output destination of the image information is selected so as to cause the internal image processing apparatus to perform a process that can be performed in a relatively short time period, and also to cause the external image processing apparatus to perform a relatively detailed process that requires high reliability, thereby achieving a reliable, conclusive diagnosis while also securing real-time performance and high-speed performance, as necessary.

Second Embodiment

Figure 3:
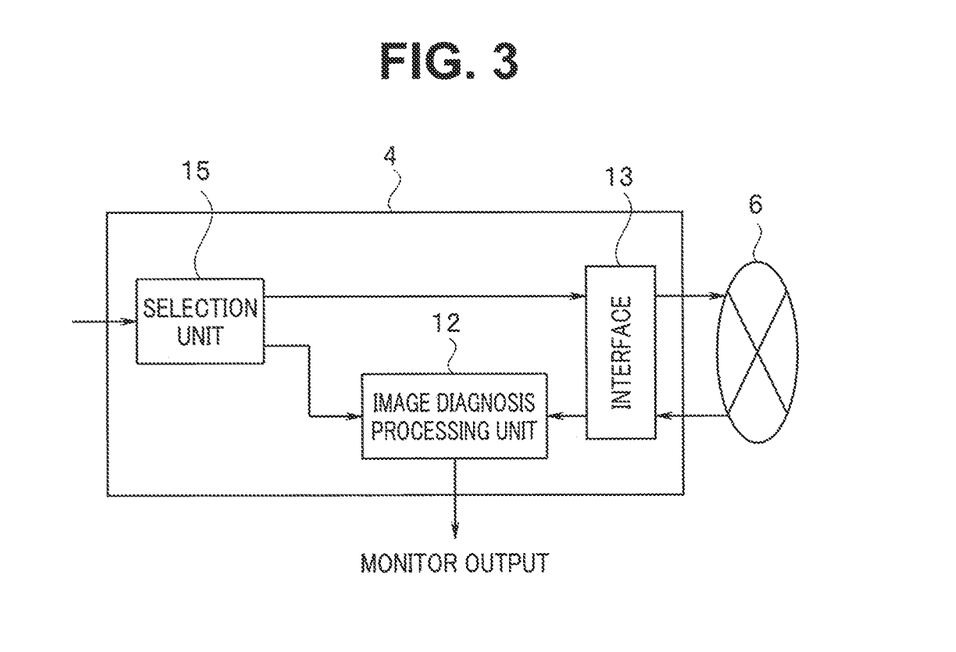
FIG. 3 is a block diagram illustrating a second embodiment of the present invention.

FIG. 3 is a block diagram illustrating a second embodiment of the present invention. FIG. 3 illustrates another specific example of the internal image processing apparatus 4, and the overall configuration of the endoscope system is similar to FIG. 1. In FIG. 3, components which are the same as FIG. 2 are denoted with the same signs, and further description is omitted.

The first embodiment describes an example of selecting the image information to be supplied to the external image processing apparatus 7 according to a selection signal based on a user operation. In contrast, the present embodiment is an example of selecting the image information to be supplied to the external image processing apparatus 7 according to signal processing performed on inputted image information.

The internal image processing apparatus 4 in the present embodiment differs from the first embodiment by adopting a selection unit 15 instead of the switch 11. The selection unit 15 acts as a selection processing unit, and selects the image information to be supplied to the external image processing apparatus 7 on the basis of inputted image information.

Figure 4:
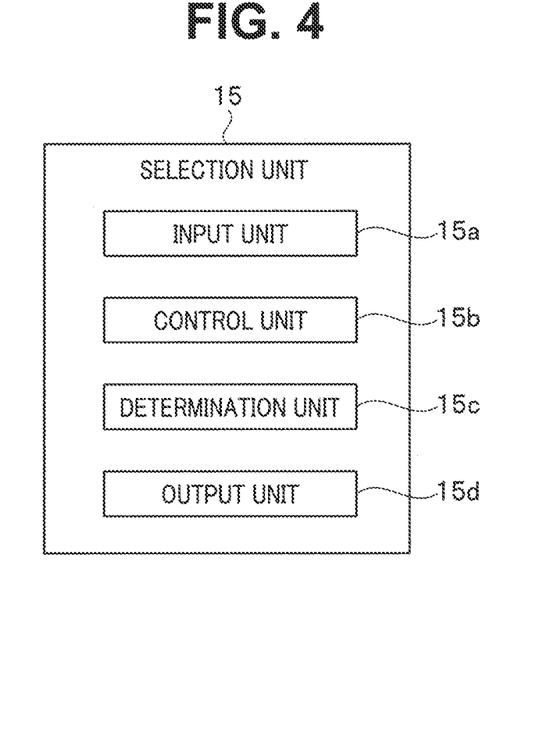
FIG. 4 is a block diagram illustrating an example of a specific configuration of a selection unit 15 in FIG. 3.

FIG. 4 is a block diagram illustrating an example of a specific configuration of the selection unit 15 in FIG. 3.

In FIG. 4, the selection unit 15 includes an input unit 15a, a control unit 15b, a determination unit 15c, and an output unit 15*d*. The control unit 15*b* and the determination unit 15*c* may include a processor using a CPU or the like and operate according to a program stored in a memory not illustrated, or achieve some or all functions in a hardware electronic circuit such as an FPGA. Note that the entire selection unit 15 may also be configured by an FPGA or the like.

The input unit 15*a* is controlled by the control unit 15*b* to acquire a medical image inputted through the central processor 3. The output unit 15*d* outputs the medical image acquired by the input unit 15*a* to the image diagnosis processing unit 12 or the interface 13 according to a determination result by the determination unit 15*c*.

The determination unit 15*c* determines whether to output the inputted medical image to the image diagnosis processing unit 12 (internal processing) or to the interface 13 (external processing) depending on the signal processing with respect to the medical image inputted from the input unit 15*a*. For example, the determination unit 15*c* determines properties such as the color, brightness, and focusing state of the inputted medical image, and decides the output destination of the medical image according to the determination result. For example, in the case where the medical image contains an image portion that is outside a predetermined hue range, the determination unit 15*c* determines that external processing should be performed and supplies the medical image to the interface 13, whereas for all other hues, the determination unit 15*c* determines that internal processing should be performed and supplies the medical image to the image diagnosis processing unit 12.

As another example, the determination unit 15*c* may also determine whether an image should be processed externally on the basis of the overall brightness of the medical image, a partial brightness in the medical image, and changes in the brightness. As another example, the determination unit 15*c* may also determine whether an image should be processed externally on the basis of the overall focusing state of the medical image, a partial focusing state of the medical image, and changes in the focusing state.

In other words, the determination unit 15*c* makes determinations such as whether or not a lesion candidate likely exists and whether or not an image is difficult to diagnose according to properties such as the color, brightness, and focusing state of an inputted medical image. For example, in the case of determining that a lesion candidate likely exists according to properties such as the color, brightness, and focusing state, the determination unit 15*c* may output the medical image to the interface 13 as an image that should be processed externally. As another example, in the case where the overall brightness of the image is extremely low and diagnosis is difficult, or in the case of an image having a poor focusing state, the determination unit 15*c* may determine that diagnosis is impossible using the input image, and output the medical image to the image diagnosis processing unit 12 as an image that should be processed internally, without transmitting the medical image to the external image processing apparatus 7. Conversely, in the case of a medical image that must be diagnosed, if the overall brightness of the image is extremely low and diagnosis is difficult, or if the image has a poor focusing state, the medical image may be output to the interface 13 as an image to be processed externally in order to make an accurate diagnosis even if the processing is time-consuming.

As another example, in situations such as the case where the image changes from a completely black image to an image with color or the case where warning information is transmitted from the central processor 3, the determination unit 15*c* may output the medical image to the interface 13 as an image to be processed externally.

Note that the selection unit 15 including the determination unit 15*c* does not perform a diagnostic process on a medical image, but rather determines whether the medical image should be processed internally or processed externally according to a relatively simple process that determines properties such as the color, brightness, and focusing state, and is configurable by a processor with relatively low processing power.

Figure 5:
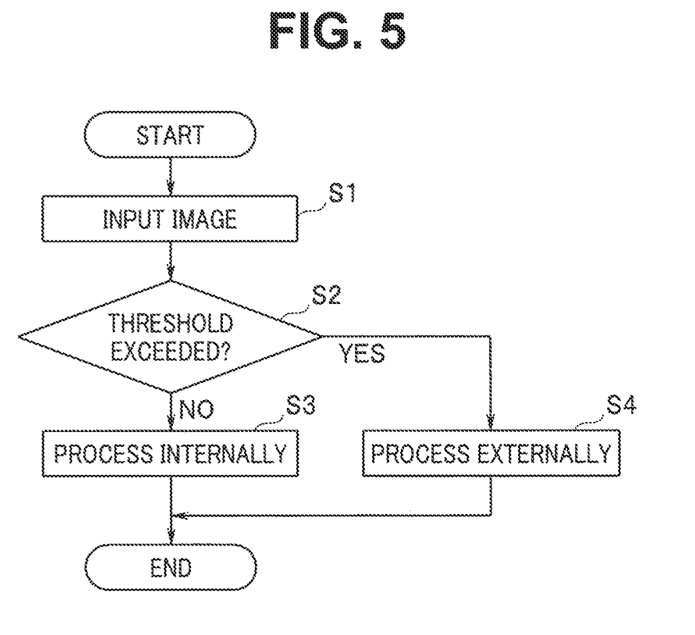
FIG. 5 is a flowchart for explaining operations by the first embodiment.

Next, operations by the embodiment configured as above will be described with reference to FIG. 5. FIG. 5 is a flowchart illustrating control by the control unit 15*b*.

A medical image from the central processor 3 is supplied to the selection unit 15 of the internal image processing apparatus 4. The control unit 15*b* included in the selection unit 15 controls the input unit 15*a* to acquire the inputted medical image (step S1). The control unit 15*b* supplies the acquired medical image to the determination unit 15*c* and the output unit 15*d*.

The determination unit 15*c* determines properties such as the color, brightness, and focusing state of the medical image to determine whether the medical image should be processed internally or externally. For example, in step S2, the determination unit 15*c* determines whether or not the brightness exceeds a predetermined threshold. For example, step S2 may determine whether the overall brightness of the medical image is a predetermined low brightness or lower, or a predetermined high brightness or higher, and in these cases, the medical image is determined to be too dark or too bright, and diagnosis is considered impossible. In such a case, the determination unit 15*c* outputs the medical image to the image diagnosis processing unit 12 to perform internal processing in step S3. Also, in the case where the overall brightness of the medical image is inside a predetermined brightness range, an accurate diagnosis is possible in the external image processing apparatus 7, and therefore in this case, the determination unit 15*c* outputs the medical image to the interface 13 to perform external processing in step S4. Note that, as described above, the determination unit 15*c* may determine that the medical image should be processed internally in the case where the overall brightness of the medical image is inside a predetermined brightness range, and determine that the medical image should be processed externally in the case where the overall brightness of the medical image is outside the predetermined brightness range.

Other operations are similar to the first embodiment.

In this way, in the present embodiment, image information to be transmitted to an external image processing apparatus is selected on the basis of signal processing performed on the medical image, and the amount of data transmitted to the external image processing apparatus can be reduced. Additionally, the output destination of the image information is selected so as to cause the internal image processing apparatus to perform a process that can be performed in a relatively short time period, and also to cause the external image processing apparatus to perform a process that requires high reliability, thereby achieving a reliable, conclusive diagnosis while also securing real-time performance and high-speed performance, as necessary.

Note that an example of selecting the image information to be transmitted to the external image processing apparatus according to image processing in a selection unit is described, but the image information to be transmitted to the external image processing apparatus may also be selected according to an image processing result in the central processor 3. In this case, the adoption of a switch similar to FIG. 2 is sufficient as the selection unit.

Note that the first and second embodiments above describe an example in which the switch 11 or the selection unit 15 selectively outputs image information to either the image diagnosis processing unit 12 or the interface 13, but in the case of outputting image information to the interface 13, the image information supplied to the interface 13 may also be supplied to the image diagnosis processing unit 12.

Third Embodiment

Figure 6:
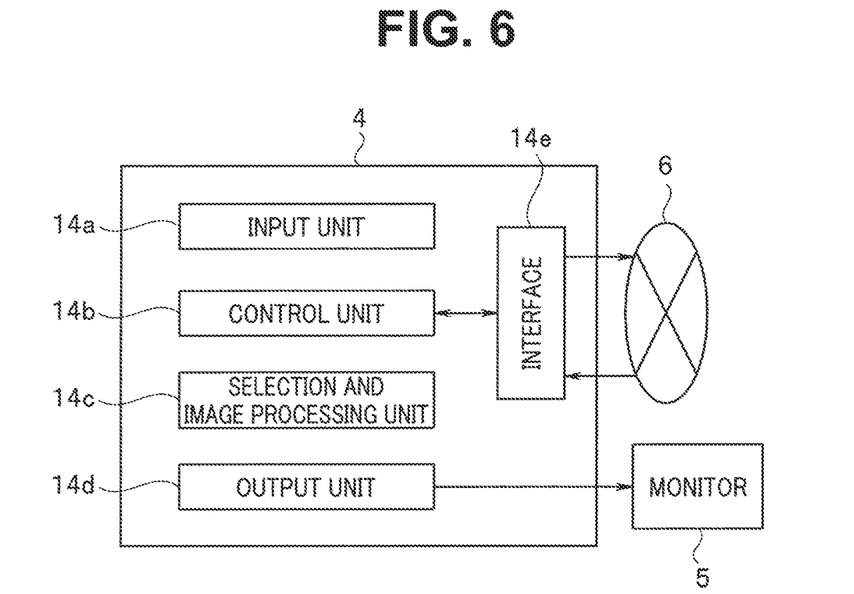
FIG. 6 is a block diagram illustrating a third embodiment of the present invention.

FIG. 6 is a block diagram illustrating a third embodiment of the present invention. FIG. 6 illustrates another specific example of the internal image processing apparatus 4, and the overall configuration of the endoscope system is similar to FIG. 1.

In FIG. 6, the internal image processing apparatus 4 includes an input unit 14a, a control unit 14b, a selection and image processing unit 14c, an output unit 14d, and an interface 14e. The internal image processing apparatus 4 in FIG. 6 has functions similar to the selection unit 15, the image diagnosis processing unit 12, and the interface 13 in FIG. 3. The input unit 14a, the control unit 14b, the output unit 14d, and the interface 14e have functions similar to the input unit 15a, the control unit 15b, the output unit 15d, and the interface 13 in FIG. 4, respectively, and the selection and image processing unit 14c has functions similar to the determination unit 15c and the image diagnosis processing unit 12.

The control unit 14b and the selection and image processing unit 14c may include a processor using a CPU or the like and operate according to a program stored in a memory not illustrated, or achieve some or all functions in a hardware electronic circuit such as an FPGA. Note that the entire internal image processing apparatus 4 in FIG. 6 may also be configured by an FPGA or the like.

The input unit 14a is controlled by the control unit 14b to acquire a medical image inputted through the central processor 3. The output unit 14d outputs the medical image acquired by the input unit 14a to the interface 14e according to a determination result by the selection and image processing unit 14c.

The selection and image processing unit 14c acts as an internal image processing unit and a selection processing unit, and determines whether to use the medical image inputted from the input unit 14a in the selection and image processing unit 14c (internal processing) or output the medical image to the interface 14e (external processing), according to signal processing performed on the medical image. Note that the determination method in the selection and image processing unit 14c is similar to the determination unit 15c, and further description is omitted.

Otherwise, the configuration and operations are similar to FIGS. 3 and 4.

In this way, in the present embodiment, effects similar to the second embodiment can also be obtained.

Fourth Embodiment

Figure 7:
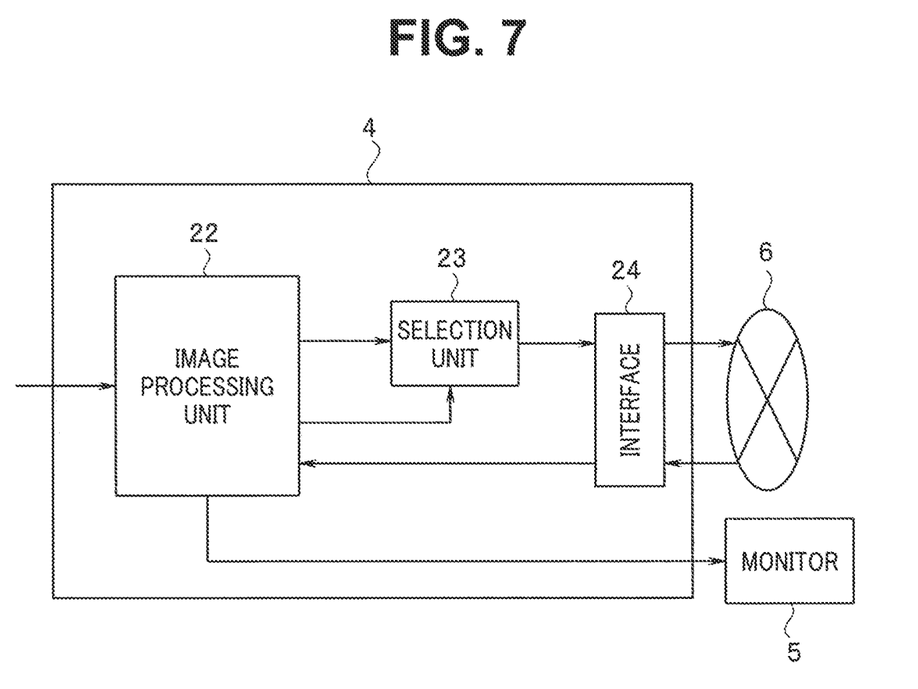
FIG. 7 is a block diagram illustrating a fourth embodiment of the present invention.

FIG. 7 is a block diagram illustrating a fourth embodiment of the present invention. FIG. 7 illustrates another specific example of the internal image processing apparatus 4, and the overall configuration of the endoscope system is similar to FIG. 1.

The first embodiment describes an example of selecting the image information to be supplied to the external image processing apparatus 7 according to a selection signal based on a user operation. In contrast, the present embodiment is an example of making a diagnosis according to image processing performed in inputted image information, and selecting the image information to be supplied to the external image processing apparatus 7 according to a diagnostic result.

In FIG. 7, the internal image processing apparatus 4 includes an image processing unit 22, a selection unit 23, and an interface 24. The image processing unit 22 acts as an internal image processing unit and a selection processing unit, making a diagnosis according to image processing performed on inputted image information, and also making a determination for selecting the image information to be supplied to the external image processing apparatus 7 according to a diagnostic result. The selection unit 23 is supplied with image information from the image processing unit 22, and outputs to the interface 24 image information determined to be processed externally according to a determination by the image processing unit 22. The interface 24 has a configuration similar to the interface 13, supplying image information from the selection unit 23 to the external image processing apparatus 7 over the external network 6, and also receiving and supplying information from the external image processing apparatus 7 over the external network 6 to the image processing unit 22.

Figure 8:
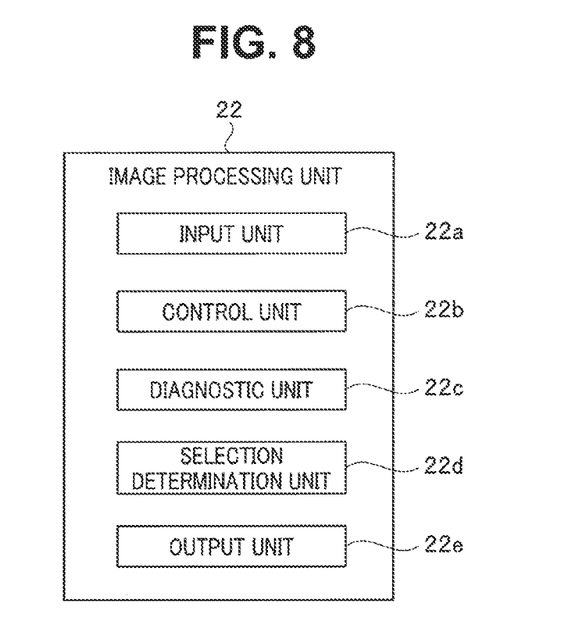
FIG. 8 is a block diagram illustrating an example of a specific configuration of an image processing unit 22 in FIG. 7.

FIG. 8 is a block diagram illustrating an example of a specific configuration of the image processing unit 22 in FIG. 7.

In FIG. 8, the image processing unit 22 includes an input unit 22a, a control unit 22b, a diagnostic unit 22c, a selection determination unit 22d, and an output unit 22e. The control unit 22b, the diagnostic unit 22c, and the selection determination unit 22d may include a processor using a CPU or the like and operate according to a program stored in a memory not illustrated, or achieve some or all functions in a hardware electronic circuit such as an FPGA. Note that the entire image processing unit 22 may also be configured by an FPGA or the like, and the entire internal image processing apparatus 4 in FIG. 7 may also be configured by an FPGA or the like.

The input unit 22a is controlled by the control unit 22b to acquire a medical image inputted through the central processor 3. The output unit 22e is controlled by the control unit 22b to output a medical image acquired by the input unit 22a to the monitor 5 directly, and also output a medical image with an attached diagnostic result from the diagnostic unit 22c to the monitor 5. In addition, the output unit 22e is controlled by the control unit 22b to output some or all of a medical image acquired by the input unit 22a to the selection unit 23.

The diagnostic unit 22c is capable of providing diagnostic support through image processing performed on a medical image inputted through the input unit 22a. For example, the diagnostic unit 22c can detect a lesion candidate on the basis of a medical image. As another example, the diagnostic unit 22c can differentiate whether a detected lesion candidate is benign or malignant.

The diagnostic unit 22c may adopt any of various known methods to detect and differentiate lesion candidates. For example, the diagnostic unit 22c may detect and differentiate lesion candidates through machine learning using AI, or detect and differentiate lesion candidates by determining respective image portions regarding properties such as color, shapes such as projections, and surface shapes through image analysis of medical images.

The selection determination unit 22d makes a selection causing a partial image of a medical image inputted by the input unit 22a to be transmitted selectively to the external image processing apparatus 7. In the present embodiment, the selection determination unit 22d uses a diagnostic result from the diagnostic unit 22c to select a medical image to be transmitted to the external image processing apparatus 7.

As described above, the external image processing apparatus 7 has functions similar to the diagnostic unit 22c, and is capable of performing more precise processing than the diagnostic unit 22c with high reliability. Accordingly, the selection determination unit 22d makes the image selection determination so as to select, and transmit to the external image processing apparatus 7, images that require a detailed and reliable diagnostic result.

For example, in the case where a lesion candidate is detectable but unidentifiable in the diagnostic unit 22c, or in the case where a lesion is identifiable but differentiation between whether the lesion is benign or malignant is not possible, the selection determination unit 22d selects an image portion containing the lesion candidate or the identified lesion to be transmitted to the external image processing apparatus 7.

The selection determination unit 22d may also generate a selection signal for supplying the external image processing apparatus 7 with an image for which the reliability of the detection result of a lesion candidate detected in the diagnostic unit 22c is lower than a predetermined threshold, or an image for which the detection of the lesion candidate itself is difficult. With the above, conclusive detection of a lesion is possible in the external image processing apparatus 7, even for images like the above. The selection determination unit 22d may also determine the size of a lesion candidate and generate a selection signal for supplying the external image processing apparatus 7 with an image containing a lesion candidate that is larger than a predetermined size. With the above, a lesion candidate of a size that raises concerns about the malignancy of the lesion can be identified and differentiated conclusively in the external image processing apparatus 7.

Furthermore, the selection determination unit 22d may generate a selection signal for selecting a frame containing a lesion candidate and a predetermined number of preceding and/or succeeding frames as images to be transmitted to the external image processing apparatus 7. With the above, transmitting a necessary and sufficient number of images enables conclusive diagnosis in the external image processing apparatus 7 and also reduces the amount of data transmitted to the external image processing apparatus 7.

The selection determination unit 22d may also not select images that are particularly difficult to diagnose in the diagnostic unit 22c as images to be transmitted to the external image processing apparatus 7, such as dark images, out-of-focus images, images blurred, and images having color or brightness that is unsuited to diagnosis. Conversely, the selection determination unit 22d may select images that should be diagnosed even if diagnosis is particularly difficult in the diagnostic unit 22c as images to be transmitted to the external image processing apparatus 7, including dark images, out-of-focus images, images blurred, and images having a color or brightness that is unsuited to diagnosis.

The selection determination unit 22d outputs a selection signal for specifying an image portion that should be selected to the selection unit 23. The selection unit 23 selects and outputs to the interface 24 only the image portion specified by the selection signal of an image supplied from the image processing unit 22.

The selection determination unit 22d may also generate a selection signal for trimming and selecting only an image portion containing a lesion candidate for example according to the selection signal. With the above, the amount of data transmitted to the external image processing apparatus 7 can be reduced.

Figure 9:
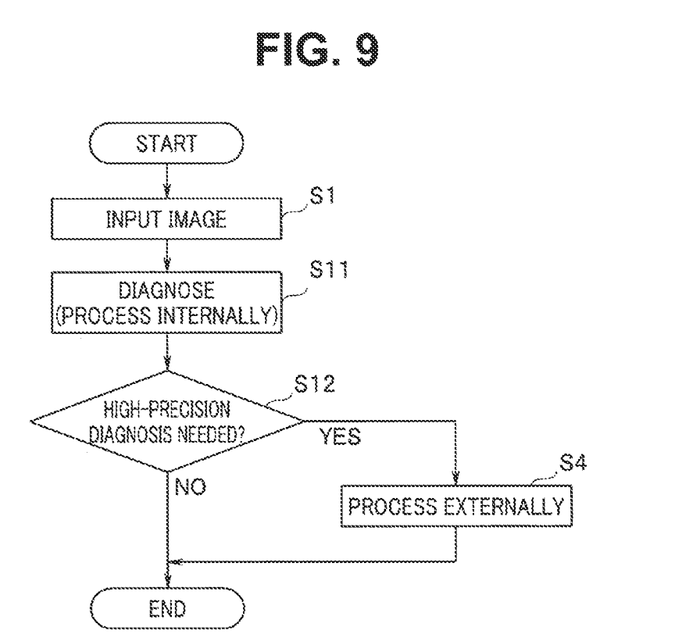
FIG. 9 is a flowchart for explaining operations by the fourth embodiment.

Next, operations by the embodiment configured as above will be described with reference to FIG. 9. FIG. 9 is a flowchart illustrating control by the control unit 22b.

Assume that the endoscope 1 is inserted into a subject, and an endoscopic image is used to detect and differentiate a lesion inside the subject. The surgeon inserts the insertion portion not illustrated into the subject not illustrated. The endoscope 1 outputs an image pickup signal obtained by shooting inside the subject to the central processor 3. The central processor 3 generates an endoscopic image based on the image pickup signal from the endoscope 1, and outputs the endoscopic image to the internal image processing apparatus 4.

The control unit 22b in FIG. 8 included in the internal image processing apparatus 4 acquires and supplies an endoscopic image to the diagnostic unit 22c in step S1 of FIG. 9. The diagnostic unit 22c performs a diagnostic process on the endoscopic image, and outputs a diagnostic result (step S11). The output unit 22e outputs the endoscopic image from the central processor 3 and the diagnostic result from the diagnostic unit 22c to the monitor 5 and causes the endoscopic image from the central processor 3 and the diagnostic result from the diagnostic unit 22c to be displayed on the display screen.

Because of limitations in processing performance, the diagnostic unit 22c is not necessarily capable of performing an accurate and precise diagnosis with real-time processing of the endoscopic image. Accordingly, the selection determination unit 22d determines whether or not a more precise diagnosis is necessary according to the diagnostic result from the diagnostic unit 22c (step S12), and if necessary, generates a selection signal for transmitting an image necessary for diagnosis to the external image processing apparatus 7.

For example, in some cases, the diagnostic unit 22c may only be able to detect a lesion candidate in real-time. If the diagnostic unit 22c detects a lesion candidate in an endoscopic image, the diagnostic unit 22c outputs a detection result to the monitor 5 through the output unit 22e. In this way, a display indicating that a lesion candidate has been detected and a display indicating the position of the lesion candidate are superimposed onto the endoscopic image and displayed on the display screen of the monitor 5 together with the endoscopic image.

Differentiation of the lesion is not performed in the diagnostic unit 22c, and therefore in step S12, the selection determination unit 22d determines that a more precise diagnosis is necessary, proceeds to step S4, and generates a selection signal causing an image portion containing the lesion candidate to be transmitted selectively.

The selection signal is supplied to the selection unit 23. The selection unit 23 selects and outputs to the interface 24 an image portion specified by the selection signal of the images from the image processing unit 22. With the above, an endoscopic image containing the lesion candidate position is outputted from the interface 24 to the external image processing apparatus 7 over the external network 6.

The external image processing apparatus 7 performs a diagnostic process on the inputted endoscopic image (step S4). The external image processing apparatus 7 is capable of high-performance processing, and can make an accurate and precise diagnosis in some cases. Through the diagnostic process performed on the image containing the lesion candidate, the external image processing apparatus 7 determines whether or not the lesion candidate is a lesion, and also differentiates the lesion. The external image processing apparatus 7 outputs a lesion detection result and differentiation result to the interface 24 over the external network 6.

The interface 24 receives and supplies the diagnostic result from the external image processing apparatus 7 to the diagnostic unit 22c. The diagnostic unit 22c outputs the reliable diagnostic result from the external image processing apparatus 7 to the monitor 5 through the output unit 22e. In this way, an endoscopic image is displayed on the display screen of the monitor 5 together with a display indicating whether or not a lesion exists in the endoscopic image, and if a lesion does exist, a display indicating the position of the lesion is also displayed. Furthermore, in the case where a differentiation result is obtained by the external image processing apparatus 7, a display indicating the lesion differentiation result is also displayed on the display screen of the monitor 5.

For example, assume that a polyp is examined. In this case, the diagnostic unit 22c detects the polyp in a short time period with a relatively simple process. As a result, a certain portion that may possibly be a polyp is displayed on the monitor 5 in near real-time. Furthermore, while the surgeon is performing an insertion operation to bring the insertion portion close to the vicinity of the polyp in order to carry out a detailed examination of the polyp, image data is transmitted to the external image processing apparatus 7, the type of polyp and the like is differentiated by a thorough diagnostic process, and the result is transmitted to the diagnostic unit 22c. With the above, an indication of whether the polyp portion is benign or malignant is displayed during the insertion operation. In other words, a cooperative diagnosis is made by the internal image processing apparatus 4 and the external image processing apparatus 7 automatically, enabling fast and conclusive diagnosis.

Note that in step S12, in the case where a precise diagnosis is not determined to be necessary by the selection determination unit 22d, a selection signal causing an image portion containing the lesion candidate to be transmitted selectively is not generated, and only internal processing is performed. In other words, in this case, only the diagnostic result from the diagnostic unit 22c is displayed on the display screen of the monitor 5.

Note that in the selection determination in step S12, the selection determination unit 22d may generate a selection signal by considering the reliability of the lesion candidate detection result, the size of the lesion candidate, the frame(s) of the image to be transmitted, whether or not the image is an image for which diagnosis is particularly difficult, and the trimming range.

In this way, in the present embodiment, effects similar to the first embodiment can also be obtained. Furthermore, in the present embodiment, the image to be transmitted to the external image processing apparatus is determined on the basis of a diagnostic result in the internal image processing apparatus, and the image that should be diagnosed in the external image processing apparatus can be selected definitively. For example, even in the case where only diagnosis prioritizing real-time performance is performed in the internal image processing apparatus, a detailed and reliable diagnosis not being performed in the internal image processing apparatus can be made conclusively in the external image processing apparatus. With the above, a detailed and reliable diagnosis can be achieved conclusively while also ensuring real-time performance and high-speed performance, as necessary.

Fifth Embodiment

Figure 10:
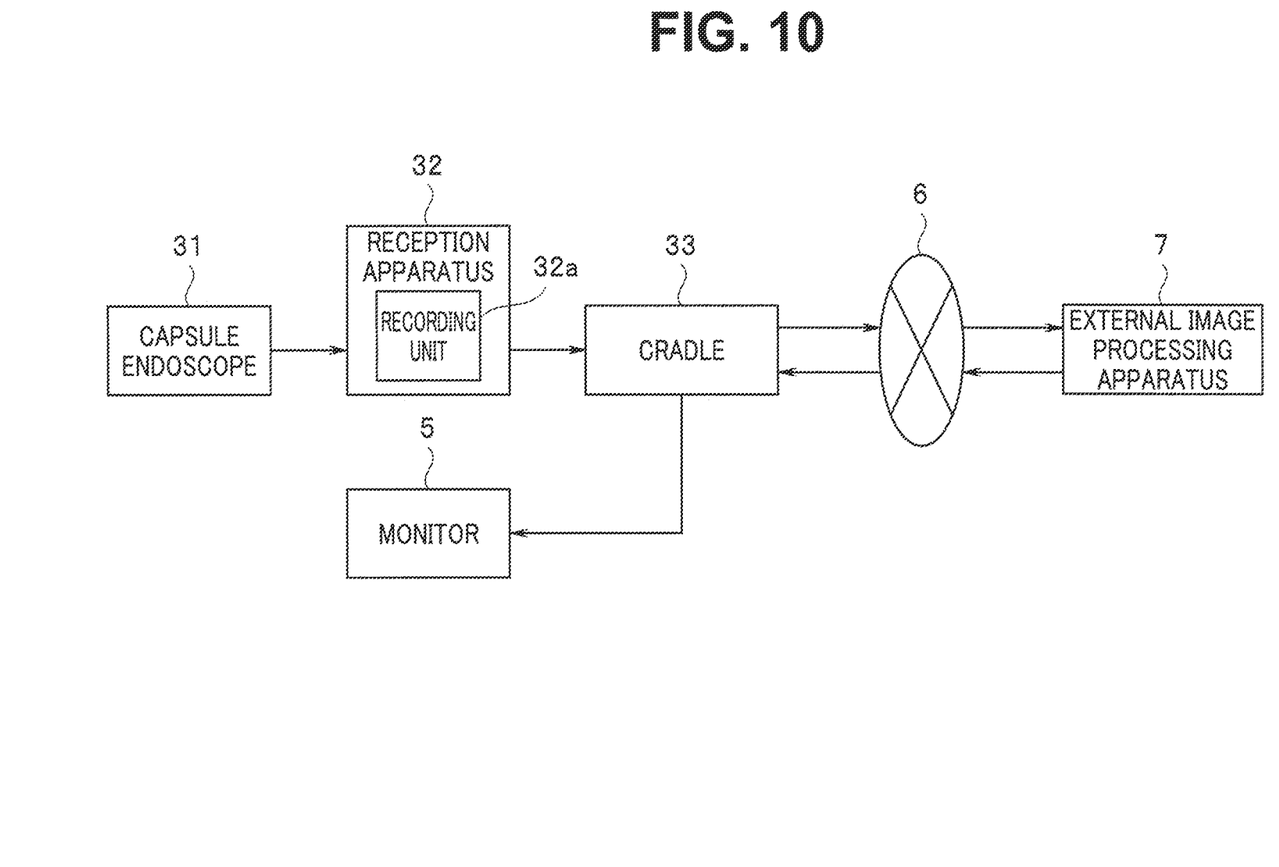
FIG. 10 is a block diagram illustrating a fifth embodiment of the present invention.

FIG. 10 is a block diagram illustrating a fifth embodiment of the present invention. In FIG. 10, components which are the same as FIG. 1 are denoted with the same signs, and further description is omitted.

Each of the foregoing embodiments describes an example of an apparatus that processes an inputted moving image in real-time, but the present embodiment is an example of an apparatus that processes a recorded moving image. As one such example, FIG. 10 illustrates an example of processing an image acquired by a capsule endoscope.

A capsule endoscope 31 is an endoscope provided with an image pickup device inside a capsule-shaped sealed container (capsule) that photographs images as the capsule is administered orally to the patient and proceeds through the patient's body. The capsule endoscope 31 wirelessly transmits endoscopic images acquired by photography to a reception apparatus 32.

The reception apparatus 32 includes a wireless transceiver, and is provided with a receiving function that receives images from the capsule endoscope 31. The reception apparatus 32 is also provided with a recording unit 32a, and receives and records endoscopic images transmitted from the capsule endoscope 31 to the recording unit 32a. The recording unit 32a includes a recording medium not illustrated, and records endoscopic images obtained by the capsule endoscope 31 performing image pickup. The reception apparatus 32 can be placed in a cradle 33, and the cradle 33 is capable of charging the reception apparatus 32.

In the present embodiment, the cradle 33 includes an internal image processing unit, and besides the function of charging the reception apparatus 32, the cradle 33 is provided with a function of reading out and acquiring images recorded to the recording unit 32a, a function of diagnosing an acquired image, a function of selecting and transmitting an image to the external image processing apparatus 7 from among the acquired images, a function of receiving a diagnostic result, and a function of outputting an acquired image and the diagnostic result to the monitor 5.

For example, the cradle 33 has a configuration similar to the image processing unit 22, the selection unit 23, and the interface 24 in FIG. 7, and of these, the image processing unit 22 has a configuration similar to the input unit 22a, the control unit 22b, the diagnostic unit 22c, the selection determination unit 22d, and the output unit 22e in FIG. 8.

In other words, the cradle 33 can acquire and diagnose images from the recording unit 32a. Note that diagnosis by the cradle 33 may be a relatively simple diagnosis comparable to the diagnosis by the diagnostic unit 22c, and may simply be a diagnosis regarding whether or not a lesion candidate exists, for example. The cradle 33 selects only images in which a lesion candidate appears according to the result of the diagnosis as images to be transmitted to the external image processing apparatus 7. The cradle 33 outputs only the selected images to the external image processing apparatus 7 over the external network 6.

Otherwise, the configuration and operations are similar to the fourth embodiment.

Generally, an enormous number of images are photographed by the capsule endoscope 31, and obtaining a detailed diagnostic result in a relatively short time period for all of the data would require an extremely powerful image processing apparatus (computer). In many cases, installing such an image processing apparatus in the examination room or the like is difficult. Accordingly, it is conceivable to transmit an image acquired by the capsule endoscope 31 over the external network 6 to the external image processing apparatus 7 having high processing power to make a diagnosis. In this case, the present embodiment is configured such that only images in which a lesion candidate exists are transmitted to the external image processing apparatus 7 from among the enormous number of endoscopic images, thereby reducing the amount of transmitted data significantly.

Note that the cradle 33 may also receive a diagnostic result from the external image processing apparatus 7 over the external network 6, and display the diagnostic result together with an endoscopic image on the monitor 5.

In this way, in the present embodiment, like the fourth embodiment, the images to be transmitted to the external image processing apparatus are determined on the basis of a diagnostic result in the cradle such that only images that should be diagnosed in the external image processing apparatus are transmitted, and the amount of transmitted data can be reduced significantly.

Sixth Embodiment

Figure 11:
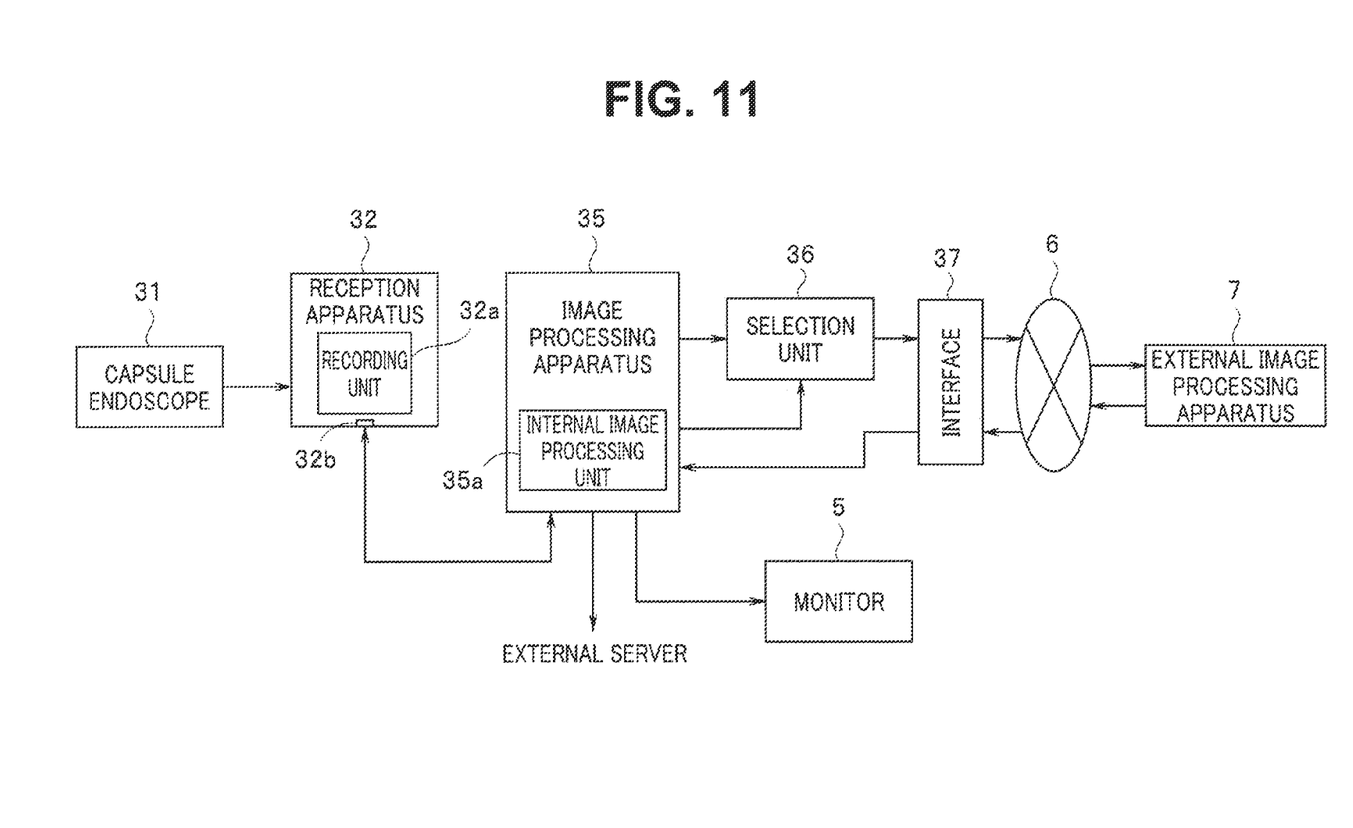
FIG. 11 is a block diagram illustrating a sixth embodiment of the present invention.

FIG. 11 is a block diagram illustrating a sixth embodiment of the present invention. In FIG. 11, components which are the same as FIG. 10 are denoted with the same signs, and further description is omitted.

The present embodiment differs from the fifth embodiment by adopting an image processing apparatus 35, a selection unit 36, and an interface 37 instead of the cradle 33. The reception apparatus 32 is provided with an interface 32b configured to transmit images recorded to the recording unit 32a. A universal serial bus (USB) port, a wireless interface, or the like can be adopted as the interface 32b. The image processing apparatus 35 includes an internal image processing unit 35a. The internal image processing unit 35a acquires and diagnoses an image recorded to the recording unit 32a through the interface 32b. Note that the internal image processing unit 35a may detect and differentiate lesion candidates through machine learning using AI, or detect and differentiate lesion candidates by determining respective image portions regarding properties such as color, shapes such as projections, and surface shapes through image analysis of medical images, for example.

In the present embodiment, the image processing apparatus 35 selects an image to be transmitted to the external image processing apparatus 7 according to a diagnostic result by the internal image processing unit 35a. In other words, the image processing apparatus 35 has a configuration similar to the selection determination unit 22d in FIG. 8. In the case of determining that a more precise diagnosis than the diagnosis by the internal image processing unit 35a is necessary, such as in the case of differentiating a lesion candidate detected by the internal image processing unit 35a, the image processing apparatus 35 generates a selection signal causing an image portion containing the lesion candidate to be transmitted selectively. The selection signal is supplied to the selection unit 36.

The selection unit 36 selects and outputs to the interface 37 an image portion specified by the selection signal of the images from the image processing apparatus 35. The interface 37 has a configuration similar to the interface 24 in FIG. 7, transmitting an image from the selection unit 36 to the external image processing apparatus 7 over the external network 6, and also receiving and outputting a diagnostic result from the external image processing apparatus 7 over the external network 6 to the image processing apparatus 35.

With the above, an endoscopic image containing the lesion candidate position is outputted from the interface 37 to the external image processing apparatus 7 over the external network 6, and a differentiation result from the external image processing apparatus 7 is received by the interface 37 and supplied to the image processing apparatus 35.

The image processing apparatus 35 can cause the endoscopic image and either or both of the processing result from the internal image processing unit 35a and the processing result received through the interface 37 to be outputted to the monitor 5 and displayed. The image processing apparatus 35 may also output the processing result to the reception apparatus 32, or transmit the endoscopic image and either or both of the processing result from the internal image processing unit 35a and the processing result received through the interface 37 to an external server not illustrated.

Otherwise, the configuration and operations are similar to the fifth embodiment.

In this way, in the present embodiment, like the fifth embodiment, only images that should be diagnosed in the external image processing apparatus can be selected and transmitted, and the amount of transmitted data can be reduced significantly. Additionally, in the present embodiment, an existing diagnostic apparatus can be used, and the endoscope system can be constructed relatively easily.

The present invention is not solely limited to the foregoing embodiments, and may be realized by modifying components within a scope that does not depart from the gist of the present invention. In addition, various inventions can be formed by appropriately combining a plurality of the components disclosed in the respective embodiments described above. For example, some of the components illustrated in an embodiment may be removed. Furthermore, components from different embodiments may also be combined appropriately.

For example, a frame containing a lesion candidate and a predetermined number of preceding and/or succeeding frames may be transmitted as images to be transmitted to the external image processing apparatus 7. With the above, transmitting a necessary and sufficient number of images enables conclusive diagnosis in the external image processing apparatus 7 and also reduces the amount of data transmitted to the external image processing apparatus 7.

Among the technologies described herein, many of the controls and functions mainly described by flowcharts can be set by a program, such that the controls and functions described above can be achieved by a computer reading out and executing the program. The program may be recorded or stored wholly or partially as a computer program product on a portable medium such as a flexible disk, a CD-ROM disc, or a non-volatile memory, or on a storage medium such as a hard disk or a volatile memory, and may also be distributed or provided at the time of product shipment, or via a portable medium or a communication channel. A user may download the program over a communication network and install the program onto a computer, or install the program onto a computer from a recording medium, and thereby achieve an endoscope system according to the embodiments easily.

What is claimed is:

1. An image processing apparatus for use with an endoscope system, the image processing apparatus comprising:

a first processor configured to:
perform image processing on an inputted image, the image processing including a diagnostic process;
a second processor configured to perform selection processing to select and transmit a portion of the inputted image to an external image processing apparatus connected to an external network;
an interface configured to receive a processing result of the diagnostic process by the external image processing apparatus; and
outputs the inputted image and at least one of the processing result by the first processor or the processing result by the external image processing apparatus.

2. The image processing apparatus used in an endoscope system according to claim 1, wherein
the second processor is configured to perform the selection processing on a basis of an operation signal to select whether to supply the inputted image to the first processor or transmit the selected portion of the inputted image to the external image processing apparatus.

3. The image processing apparatus used in an endoscope system according to claim 1, wherein
the second processor is configured to perform the selection processing on a basis of signal processing performed on the inputted image to select whether to supply the inputted image to the first processor or transmit the selected portion of the inputted image to the external image processing apparatus.

4. The image processing apparatus used in an endoscope system according to claim 1, wherein
the second processor is configured to perform selection processing to select an image to be transmitted to the external image processing apparatus of the image inputted into the first processor.

5. The image processing apparatus used in an endoscope system according to claim 1, wherein
the second processor is configured to perform selection processing to select an image to be transmitted to the external image processing apparatus on a basis of a processing result of an image processing performed by the first processor.

6. The image processing apparatus used in an endoscope system according to claim 1, wherein
the first processor is configured to at least one of a detection of a lesion candidate or a differentiation of the lesion candidate.

7. The image processing apparatus used in an endoscope system according to claim 1, wherein
the external image processing apparatus is configured to perform at least one of a detection of a lesion candidate or a differentiation of the lesion candidate.

8. The image processing apparatus used in an endoscope system according to claim 1, wherein
the first processor and the external image processing apparatus are configured to perform at least one of a detection of a lesion candidate or a differentiation of the lesion candidate.

9. The image processing apparatus used in an endoscope system according to claim 1, wherein
the first processor is configured to output a processing result in a short time period compared to the external image processing apparatus.

10. The image processing apparatus used in an endoscope system according to claim 1, wherein
the external image processing apparatus is configured to output a detailed processing result compared to the first processor.

11. The image processing apparatus used in an endoscope system according to claim 1, wherein
the first processor is configured to make a first diagnosis with respect to the inputted image, and
the second processor is configured to select, on a basis of a result of the first diagnosis, an image used by the external image processing apparatus to make a second diagnosis more detailed than the first diagnosis.

12. The image processing apparatus used in an endoscope system according to claim 1, wherein
the first processor is configured to detect a lesion candidate from the inputted image,
the second processor is configured to select an image to selectively transmit an image containing an image portion of the lesion candidate to cause the external image processing apparatus to differentiate the lesion candidate, and
the interface is configured to receive a differentiation result of the lesion candidate based on the image processor by the external image processing apparatus as the processing result.

13. The image processing apparatus used in an endoscope system according to claim 1, wherein
the second processor is configured to perform selection processing to transmit a trimmed image having an image portion containing a lesion candidate to the external image processing apparatus.

14. The image processing apparatus used in an endoscope system according to claim 1, wherein
the second processor is configured to perform selection processing to transmit an image having a detection reliability of the lesion candidate that is lower than a predetermined threshold to the external image processing apparatus, and
the interface is configured to receive the processing result based on the image having the detection reliability of the lesion candidate that is lower than the predetermined threshold transmitted from the second processor to the external image processing apparatus.

15. The image processing apparatus used in an endoscope system according to claim 1,
wherein the second processor is configured to perform selection processing to transmit an image having a size of an image portion of the lesion candidate that is larger than a predetermined size to the external image processing apparatus.

16. The image processing apparatus used in an endoscope system according to claim 1, wherein
the second processor is configured to perform selection processing to transmit images of a frame containing the lesion candidate and a predetermined number of preceding and/or succeeding frames of the frame containing the lesion candidate to the external image processing apparatus.

17. The image processing apparatus used in an endoscope system according to claim 1, wherein
in a case where at least one of a brightness range, a color range, or a focusing state range of the inputted image is outside a respective threshold range, the second processor is configured to perform selection processing to not transmit the inputted image to the external image processing apparatus.

18. The image processing apparatus used in an endoscope system according to claim 1, wherein the image processing apparatus outputs the inputted image and at least one of the processing result by the first processor or the processing result by the external image processing apparatus to a monitor.

19. The image processing apparatus used in an endoscope system according to claim 2, wherein
the second processor is configured to perform the selection processing on a basis of an operation signal based on an operation of at least one of photographing a still image, generating a still image, switching an observation mode, enlarging an image, pausing an image for a predetermined time period or longer, or turning a piece of medical equipment on or off.

20. An endoscope system comprising:
the image processing apparatus used in an endoscope system according to claim 1; and
the external image processing apparatus.

21. An image processing method used in an endoscope system comprising:
performing image processing on an inputted image, the image processing including a diagnostic process;
performing selection processing to select and transmit a portion of the inputted image to an external image processing apparatus connected to an external network;
receiving a processing result of the diagnostic process by the external image processing apparatus; and
outputting the inputted image and at least one of the processing result by the first processor or the processing result by the external image processing apparatus.

* * * * *